United States Patent
Kumar et al.

(10) Patent No.: US 11,318,183 B2
(45) Date of Patent: May 3, 2022

(54) STABLE PHARMACEUTICAL COMPOSITION OF VASOPRESSIN

(71) Applicant: MANKIND PHARMA LTD., New Delhi (IN)

(72) Inventors: Saurabh Kumar, Gurugram (IN); Ankush Gupta, Gurugram (IN); Hanumant Gambhire, Gurugram (IN); Raghuveera H. G, Gurugram (IN); P. V. S Narasimham, Gurugram (IN); Anil Kumar, Gurugram (IN)

(73) Assignee: Mankind Pharma Ltd., New Delhi (IN)

( * ) Notice: Subject to any disclaimer, the term of this patent is extended or adjusted under 35 U.S.C. 154(b) by 0 days.

(21) Appl. No.: 16/981,892

(22) PCT Filed: Mar. 15, 2019

(86) PCT No.: PCT/IB2019/052117
§ 371 (c)(1),
(2) Date: Sep. 17, 2020

(87) PCT Pub. No.: WO2019/180561
PCT Pub. Date: Sep. 26, 2019

(65) Prior Publication Data
US 2021/0008152 A1    Jan. 14, 2021

(30) Foreign Application Priority Data

Mar. 20, 2018 (IN) .............. 201811010144

(51) Int. Cl.
*A61K 38/095* (2019.01)
*A61P 9/02* (2006.01)
*A61K 47/12* (2006.01)
*A61K 47/18* (2017.01)

(52) U.S. Cl.
CPC ............ *A61K 38/095* (2019.01); *A61K 47/12* (2013.01); *A61K 47/183* (2013.01); *A61P 9/02* (2018.01)

(58) Field of Classification Search
CPC .... A61K 38/095; A61K 47/12; A61K 47/183; A61K 9/0019; A61P 9/02
See application file for complete search history.

(56) References Cited

U.S. PATENT DOCUMENTS

| | | |
|---|---|---|
| 5,482,931 A | 1/1996 | Harris et al. |
| 5,763,405 A * | 6/1998 | Fjellestad-Paulsen ...................... A61K 9/5078 514/10.9 |
| 6,949,509 B2 | 9/2005 | Woodrow |
| 9,375,478 B1 * | 6/2016 | Kenney ................. A61K 47/10 |
| 9,744,239 B2 | 8/2017 | Kenney et al. |
| 2011/0237508 A1 | 9/2011 | Amorij et al. |
| 2017/0354708 A1 | 12/2017 | Kenney et al. |
| 2018/0015168 A1 | 1/2018 | Soane et al. |

FOREIGN PATENT DOCUMENTS

WO    1995025534    9/1995

OTHER PUBLICATIONS

Vaspressin_FDA_ChemicalReviews 2014 (Year: 2014).*
International Search Report, issued in the corresponding PCT application No. PCT/IB2019/052117, dated Jun. 27, 2019, 3 pages.

* cited by examiner

*Primary Examiner* — Sudhakar Katakam
(74) *Attorney, Agent, or Firm* — Hamre, Schumann, Mueller & Larson, P.C.

(57) ABSTRACT

The present invention relates to a stable pharmaceutical composition comprising vasopressin or pharmaceutically acceptable salts thereof. The present invention further provides a method of increasing blood pressure in adults with vasodilatory shock by administering said pharmaceutical composition of vasopressin or pharmaceutically acceptable salts thereof.

12 Claims, No Drawings

STABLE PHARMACEUTICAL COMPOSITION OF VASOPRESSIN

FIELD OF THE INVENTION

The present invention relates to a stable pharmaceutical composition comprising vasopressin or pharmaceutically acceptable salts thereof.

BACKGROUND OF THE INVENTION

Vasopressin is a polypeptide hormone. Vasopressin contains nine amino acids, with a disulfide bridge between cysteine residues. Chemically vasopressin is cyclo(1-6)-L-cysteinyl-L-tyrosyl-L-phenylalanyl-L-glutaminyl-L-asparaginyl-L-cysteinyl-L-propyl-L-arginyl-L-glycinamide.

Vasopressin is indicated to increase blood pressure in adults with vasodilatory shock (e.g. postcardiotomy or sepsis) who remain hypotensive despite fluids and catecholamines. It is available under the trade name of Vasostrict® Solution; Intravenous (IV) for Infusion with of 3.8 and supplied as 20 units/ml and 200 units/10 ml.

U.S. Pat. No. 9,375,478 and its family discloses a pharmaceutical composition comprising vasopressin and a buffer having acidic pH. It also discloses that greatest level of stability of vasopressin formulation was observed at pH 3.5. However, the formulation claimed in US '478 patent is having pH of 3.8.

US Pub. No. 2017/0354708 A1 discloses pharmaceutical composition comprising vasopressin, or a pharmaceutically-acceptable salt thereof; and a polymeric pharmaceutically-acceptable excipient. It also discloses that vasopressin assay in the vasopressin formulations with citrate buffer is lower than in the vasopressin formulations with acetate buffer. It also discloses that vasopressin formulations are stable at pH values in the range of 3.5 to 4.5. The results of the experiments suggested that the stability of a vasopressin formulation was highest between pH 3.6 and pH3.8.

U.S. Pat. No. 9,744,239 discloses a method of increasing blood pressure with a unit dosage form of vasopressin, wherein the unit dosage form is diluted in 0.9% saline or 5% dextrose in water to provide a concentration from about 0.1 units/mL to about 1 unit/mL of vasopressin and administering the diluted unit dosage form to the human by intravenous administration.

US Pub. No. 2018/0015168 A1 discloses therapeutic formulation comprising a protein active ingredient and a stabilizing excipient such as polypropylene glycol homopolymer.

U.S. Pat. No. 6,949,509 discloses stable composition of vasopressin free of preservatives wherein the composition has a pH between 3.5 and 6.

U.S. Pat. No. 5,482,931 discloses aqueous composition for administration of small and medium-size peptides comprising buffer, a quaternary amine preservative or disinfectant and an osmotic pressure-controlling agent. It also discloses pH of the composition between about 4 and 6.

US Pub. No. 2011/0237508 discloses formulation comprising vasopressin or an analogue thereof, a buffer and at least one non-toxic source of divalent metal ions in a concentration of at least 2 mM. It further discloses that such formulation is having a pH between 3 and 6, preferably between 3 and 5, more preferably between 3.8 and 4.8.

Aqueous formulations of therapeutic peptides are susceptible to degradation through a number of different mechanisms and as a result of several types of stress conditions like freeze/thaw cycles, agitation, long term storage, pumping, filtration, or unrefrigerated storage.

Peptides can undergo deamidation during which an amide group is removed from an amino acid, and can be associated with protein degradation, apoptosis, and other regulatory functions within the cell. The susceptibility to deamidation can depend on primary sequence of the protein, three-dimensional structure of the protein, and solution properties including, for example, pH, temperature, ionic strength, and buffer ions. Deamidation can be catalyzed by acidic conditions.

In view of the above, it is therefore desirable to provide a stable pharmaceutical composition of therapeutic peptides to make the therapeutic peptides more resistant to demidation and the stress conditions encountered during their distribution and storage. Applicant has developed a composition of vasopressin which is having pH less than or equal to 3.6 and is still stable with total impurities less than 5% upon storage at 2 to 8° C.

SUMMARY OF THE INVENTION

The present invention relates to a stable aqueous composition for administration of small and medium-size peptides, particularly vasopressin, which can maintain stability during its storage.

According to one aspect, the present invention provides a stable pharmaceutical composition comprising vasopressin or a pharmaceutically acceptable salt thereof and one or more pharmaceutically acceptable excipients.

According to one embodiment, the pharmaceutical composition is in the form of aqueous solution or a lyophilized powder, which can be diluted or reconstituted just prior to use.

According to another embodiment, the pharmaceutical composition is in the form of ready to use composition.

According to another embodiment, the present invention provides a stable pharmaceutical composition comprising vasopressin or a pharmaceutically acceptable salt thereof and one or more pharmaceutically acceptable excipients, wherein the one or more pharmaceutically acceptable excipients are selected from the group comprising buffering agents, tonicity agents, pH adjusting agents, preservatives, vehicles, hulking agents and lyoprotectants and/or combinations thereof.

According to another embodiment, the present invention provides a stable pharmaceutical composition comprising vasopressin or a pharmaceutically acceptable salt thereof and one or more pharmaceutically acceptable excipients, wherein the composition has pH in the range of 2.4 to 3.6, preferably in the range of 2.8 to 3.2.

According to another embodiment, the present invention provides a stable pharmaceutical composition comprising vasopressin or a pharmaceutically acceptable salt thereof and one or more pharmaceutically acceptable excipients, wherein the composition has less than 5% total impurities upon storage at 2 to 8° C.

According to another embodiment, the present invention provides a stable pharmaceutical composition comprising vasopressin or a pharmaceutically acceptable salt thereof and pharmaceutically acceptable excipients which is useful for increasing blood pressure in adults with vasodilatory shock.

DESCRIPTION OF THE INVENTION

The present invention relates to a stable aqueous composition or administration of small and medium-size peptides, particularly vasopressin, which can maintain stability during its storage.

Applicant has developed a stable pharmaceutical composition of vasopressin which can encounter stress conditions like freeze/thaw cycles, agitation, long term storage, pumping, filtration, or unrefrigerated storage. Applicant has developed a stable composition of vasopressin having lower pH compared to prior art compositions having higher pH range.

While working on the present invention inventors have developed a stable pharmaceutical composition of vasopressin with glycine buffer. The formulation showed maximum stability in the pH range of 2.4 to 3.6.

The pharmaceutical composition as pet the present invention comprises vasopressin or a pharmaceutically-acceptable salt thereof and pharmaceutically acceptable excipients, wherein the pharmaceutical composition comprises from about 0.01 mg/mL to about 0.07 mg/mL of vasopressin or pharmaceutically acceptable salts thereof.

The pharmaceutical composition is suitable for parenteral administration to a patient. The pharmaceutical compositions can be in a form suitable for parenteral injection such as a sterile suspension, solution, or emulsion in oily or aqueous vehicles.

The pharmaceutical composition as per the present invention may be filled into single dose vial or multi dose vial. The pharmaceutical composition is free from preservatives when filled into a multi-dose vial/container.

The pharmaceutical composition as per the present invention comprises therapeutically effective amount of vasopressin or pharmaceutically acceptable salts thereof and one or more pharmaceutically acceptable excipients, wherein the one or more pharmaceutically acceptable excipients are selected from the group comprising buffering agents, tonicity agents, pH adjusting agents, preservatives, vehicles, bulking agents and lyoprotectants and/or combinations thereof.

Suitable buffering agent may include one or more of buffers such as, for example, citrate, phosphate, tris HCl, acetic acid, sodium acetate, amino acids such as glycine, aspartate/aspartic acid, histidine, cysteine, tyrosine, phenylalanine, proline, arginine, threonine, serine, valine, isoleucine, lysine and glutamine. More preferably, the present invention comprises glycine as a buffer in a concentration of between 0.006 mM to 0.16 mM.

In an embodiment of the present invention, there is provided a pharmaceutical composition comprising vasopressin or a pharmaceutically-acceptable salt thereof and a buffer having acidic pH.

In another embodiment of the present invention, there is provided a pharmaceutical composition comprising vasopressin or a pharmaceutically-acceptable salt thereof, wherein the pharmaceutical composition is free of acetate buffer.

In another embodiment of the present invention, the composition of the present invention has a pH in the range of 2.4 to 3.6. Preferably, the composition has a pH in the range of 2.8 to 3.2.

In another embodiment of the present invention, the composition of the present invention has glycine as a buffering agent and has a pH in the range of 2.8 to 3.2.

In another embodiment of the present invention, the composition of the present invention has sodium acetate as a buffering agent.

In another embodiment of the present invention, the composition of the present invention has aspartic acid as a buffering agent.

In another embodiment, the suitable pH adjusting agent include hydrochloric acid, sodium hydroxide, and succinic acid.

In another embodiment, suitable vehicles are selected from the group comprising water for injection, ethanol, glycerin, propylene glycol, corn oil, peanut oil, and cotton seed oil.

In another embodiment, suitable tonicity agents include dextrose, glycerol, sodium chloride, potassium chloride, glycerine, and mannitol.

In another embodiment, suitable preservative is selected from benzyl alcohol, parabens (methyl, propyl, butyl), benzalkonium chloride, chlorobutanol, and thiomersal.

In another embodiment, suitable lyoprotectants include sucrose, trehalose, mannitol, glycine, lysine and dextran.

In another embodiment, suitable bulking agents include sucrose, lactose, trehalose, mannitol, sorbitol, glucose, PVP, and hydroxyethyl starch.

In a preferred embodiment of the present invention, the pharmaceutical composition comprises of about 0.01 mg/mL to about 0.07 mg/mL of vasopressin, about 0.01 mg/ml to about 20 mg/ml of glycine buffer, water for injection and the said composition is adjusted with 0.1 N HCl or sodium hydroxide to pH of about 2.8 to 3.2.

In one another embodiment, the present invention provides a stable pharmaceutical composition comprising vasopressin or a pharmaceutically-acceptable salt thereof and one or more pharmaceutically acceptable excipients, wherein the pharmaceutical composition is in the form of ready to use composition.

In one another embodiment, the present invention provides a pharmaceutical composition comprising vasopressin or a pharmaceutically-acceptable salt thereof and pharmaceutically acceptable excipients, wherein the pharmaceutical composition is in the form of aqueous solution or a lyophilized powder, which can be diluted or reconstituted just prior to use.

In one another embodiment, the present invention further provides a stable pharmaceutical composition comprising vasopressin or a pharmaceutically-acceptable salt thereof and one or more pharmaceutically acceptable excipients, wherein the composition has total impurities less than 10% upon storage at 2 to 8° C., preferably less than 5%.

The pharmaceutical compositions as per the present invention can be sterilized using any of the known methods of sterilization, such as filtration, moist heat, dry heat, gas sterilization or irradiation (gamma and electron beam), preferably by filtration. The container in which composition is filled can be sterilized using gamma irradiation or ethylene oxide or pre-acetic acid or any other conventional method of sterilization.

The present invention is further illustrated by the following examples which are provided merely to be exemplary of the invention and don't limit the scope of the invention. Certain modifications and equivalents will be apparent to those skilled in the art and are intended to be included within the scope of the present invention.

EXAMPLE 1

| Ingredient | Quantity | |
| --- | --- | --- |
|  | mg/mL | % w/v |
| Vasopressin | 20IU equivalent to 0.045 | 0.0045 |
| Glycine | 0.45 | 0.045 |
| Hydrochloric Acid/ Sodium hydroxide | q.s. to pH range 2.4 to 3.6 | q.s. to pH range 2.4 to 3.6 |
| Water for Injection | q.s. | q.s. |

Process:
1. Collecting 80% of water for injection and cooling it to room temperature (20-25° C.).
2. Adding glycine in above collected water, and keep stirring till clear solution is formed.
3. Adjusting the pH with hydrochloric acid or sodium hydroxide in the range of 2.4 to 3.6.
4. Adding Vasopressin in step 3 solution and keep stirring till clear solution is formed.
5. Making up the volume to 100% batch size.
6. Filtering the solution and then filling in a glass vial.
7. Storing the solution at 2-8° C.

EXAMPLE 2

| Ingredient | Quantity mg/mL | % w/v |
|---|---|---|
| Vasopressin | 20IU equivalent to 0.045 | 0.0045 |
| Glycine | 0.90 | 0.090 |
| Hydrochloric Acid/ Sodium hydroxide | q.s. to pH range 2.8 to 3.2 | q.s. to pH range 2.8 to 3.2 |
| Water for Injection | q.s. | q.s. |

Process:
1. Collecting 80% of water for injection and cooling it to room temperature (20-25° C.).
2. Adding glycine in above collected water, and keep stirring till clear solution is formed.
3. Adjusting the pH with hydrochloric acid or sodium hydroxide in the range of 2.8 to 3.2.
4. Adding Vasopressin in step 3 solution and keep stirring till clear solution is formed.
5. Making up the volume to 100% batch size.
6. Filtering the solution and then filling in a glass vial.
7. Storing the solution at 2-8° C.

EXAMPLE 3

| Ingredient | Quantity mg/mL | % w/v |
|---|---|---|
| Vasopressin | 20IU equivalent to 0.045 | 0.0045 |
| Glycine | 12.0 | 1.20 |
| Hydrochloric Acid/ Sodium hydroxide | q.s. to pH range 2.8 to 3.2 | q.s. to pH range 2.8 to 3.2 |
| Water for Injection | q.s. | q.s. |

Process:
1. Take approx 80% of hatch size quantity of Water for injection.
2. Add Glycine in it and stir for 20 minutes till clear solution formed. Check the pH of bulk solution.
3. Adjust the pH of solution with 0.1N hydrochloric acid or sodium hydroxide to 2.8 to 3.2.
4. Add the required quantity of vasopressin API in step 3 solution and continue stirring for 15 min or till clear solution formed.
5. Volume make up to 100% of hatch size with remaining quantity of water for injection.
6. Check the final pH of bulk solution.
7. Filter the solution through 0.22μ sterilizing grade filter.
8. Fill the solution in USP-Type-I clear glass vial and seal with 13 mm rubber stopper.

EXAMPLE 4

| Ingredient | Quantity mg/mL | % w/v |
|---|---|---|
| Vasopressin | 20IU equivalent to 0.045 | 0.0045 |
| Sodium acetate trihydrate | 1.36 | 0.136 |
| Hydrochloric Acid/ Sodium hydroxide | q.s. to pH range 2.8 to 3.2 | q.s. to pH range 2.8 to 3.2 |
| Water for Injection | q.s. | q.s. |

Process:
1. Take approx 80% of batch size quantity of Water for injection.
2. Add sodium acetate in it and stir for 20 minutes till clear solution formed. Check the pH of bulk solution.
3. Adjust the pH of solution with 0.1N hydrochloric acid or sodium hydroxide to 2.8 to 3.2.
4. Add the required quantity of vasopressin API in step 3 solution and continue stirring for 15 min or till clear solution formed. Check the pH of solution.
5. Volume make up to 100% of batch size with remaining quantity of water for injection.
6. Check the final pH of bulk solution and maintain the final pH in the range of 2.8 to 3.2.
7. Filter the solution through 0.22μ sterilizing grade filter.
8. Fill the solution in USP-Type-1 clear glass vial and seal with 13 mm rubber stopper.

EXAMPLE 5

| Ingredient | Quantity mg/mL | % w/v |
|---|---|---|
| Vasopressin | 20IU equivalent to 0.045 | 0.0045 |
| Acetic acid | q.s. | q.s. |
| Sodium hydroxide | q.s. to pH range 2.8 to 3.2 | q.s. to pH range 2.8 to 3.2 |
| Water for Injection | q.s. | q.s. |

Process:
1. Take approx 80% of hatch size quantity of Water for injection.
2. Add acetic acid in it and stir for 20 minutes till clear solution formed. Check the pH of bulk solution.
3. Adjust the pH of solution with sodium hydroxide in the range of 2.8 to 3.2.
4. Add the required quantity of vasopressin API in step 3 solution and continue stirring for 15 min or till clear solution formed. Check the pH of solution.
5. Volume make up to 100% of batch size with remaining quantity of water for injection.
6. Check the final pH of bulk solution and maintain the final pH in the range of 2.8 to 3.2.
7. Filter the solution and filled into glass vial.

EXAMPLE 6

| Ingredient | Quantity mg/mL | % w/v |
|---|---|---|
| Vasopressin | 20IU equivalent to 0.045 | 0.0045 |
| Aspartic acid | 0.30 | 0.03 |
| Sodium hydroxide | q.s. to pH range 2.8 to 3.2 | q.s. to pH range 2.8 to 3.2 |
| Water for Injection | q.s. | q.s. |

Process:
1. Take approx 80% of batch size quantity of Water for injection.
2. Add aspartic acid in it and stir for 20 minutes till clear solution formed.
3. Adjust the pH of solution with sodium hydroxide in the range of 2.8 to 3.2.
4. Add the required quantity of vasopressin API in step 3 solution and continue stirring for 15 min or till clear solution formed.
5. Volume make up to 100% of batch size with remaining quantity of water for injection.
6. Check the final pH of bulk solution and maintain the final pH in the range of 2.8 to 3.2.
7. Filter the solution and Idled into glass vial.

Stability Studies:

The pharmaceutical compositions of the present invention as prepared according to examples 3 and 4 were tested for stability for 3 months at 2 to 8° C. The results of the same are provided in table 1 below.

TABLE 1

| | Vasotrict ® | | | | | | |
|---|---|---|---|---|---|---|---|
| | | | End of Shelf | Example 3 2-8° C. | | Example 4 2-8° C. | |
| Test Parameters | Specification | Initial | life | Initial | 3M | Initial | 3M |
| Assay | 90% to 110% | 103.5 | 103.1 | 102.4 | 99.10 | 102.70 | 99.01 |
| pH | 2.5 to 4.5 | 3.90 | Not done | 2.80 | 2.90 | 2.80 | 2.90 |
| Des Pro Vasopressin | NMT 1.0% | ND | ND | 0.15 | 0.09 | 0.14 | 0.10 |
| 8 Orn Vasopressin | NMT 1.0% | 0.09 | 0.37 | 0.42 | 0.24 | 0.33 | 0.31 |
| Endo gln Vasopressin | NMT 1.0% | 0.29 | 0.22 | ND | ND | ND | ND |
| Vasopressin BIS-SH | NMT 1.0% | ND | ND | ND | ND | ND | ND |
| Vasopressin Acid | NMT 1.0% | 0.30 | 0.36 | 0.06 | 0.28 | 0.08 | 0.35 |
| 5-Asp Vasopressin | NMT 1.0% | 0.08 | 0.08 | ND | 0.1 | ND | 0.07 |
| 4-Glu Vasopressin | NMT 1.0% | 0.22 | 0.37 | 0.12 | 0.37 | 0.27 | 0.43 |
| Vasopressin Parallel Dimer | NMT 1.0% | ND | ND | ND | ND | ND | ND |
| Vasopressin Antiparallel Dimer | NMT 1.0% | ND | ND | ND | ND | ND | 0.004 |
| N-Acetyl Vasopressin | NMT 1.0% | 0.21 | 0.21 | 0.08 | 0.08 | 0.07 | 0.07 |
| Total Impurities | NMT 10% | 1.36 | 1.74 | 1.09 | 1.53 | 1.45 | 1.96 |

Results:

The vasopressin content was measured to be in range of 99.1 to 99.0 for compositions of example 3 and 4 respectively, which is in acceptable limits range (Limit 90.0-110.0%). Total impurities were measured to be 1.53% and 1.96% for compositions of examples 3 and 4 respectively which are also within the acceptable limit of NMT 10%.

Hence, it is concluded from the above stability data that the compositions prepared as per the resent invention have an unexpected enhanced stability.

The invention claimed is:

1. A pharmaceutical composition comprising vasopressin or a pharmaceutically acceptable salt thereof, 0.025% w/v to 1.25% w/v of a buffering agent, and one or more pharmaceutically acceptable excipients, wherein the pharmaceutical composition is formulated for parenteral administration and has a pH in the range of 2.8 to 3.2.

2. The pharmaceutical composition as claimed in claim 1, wherein the one or more pharmaceutically acceptable excipients are selected from, tonicity agents, pH adjusting agents, preservatives, vehicles, bulking agents, lyoprotectants, or combinations thereof.

3. The pharmaceutical composition as claimed in claim 1, wherein the buffering agent is selected from citrate, phosphate, tris HCl, acetic acid, sodium acetate, glycine, aspartic acid, histidine, cysteine, tyrosine, phenylalanine, praline, arginine, threonine, serine, valine, isoleucine, lysine, glutamine, or combinations thereof.

4. The pharmaceutical composition as claimed in claim 3, wherein the buffering agent is glycine.

5. The pharmaceutical composition as claimed in claim 3, wherein the buffering agent is sodium acetate.

6. The pharmaceutical composition as claimed in claim 3, wherein the buffering agent is aspartic acid.

7. The pharmaceutical composition as claimed in claim 1, wherein the composition has less than 5% of total impurities upon storage at 2 to 8° C.

8. The pharmaceutical composition as claimed in claim 1, wherein the composition is diluted or reconstituted just prior to use.

9. The pharmaceutical composition as claimed in claim 1, wherein the composition is in the form of ready to use composition.

10. The pharmaceutical composition as claimed in claim 1, wherein the composition is useful for increasing blood pressure in adults with vasodilatory shock.

11. The pharmaceutical composition as claimed in claim 1, wherein the composition is filled into a multiple dose vial.

12. The pharmaceutical composition as claimed in claim 9, wherein the composition is free of preservative.

* * * * *